United States Patent [19]

Tovey

[11] Patent Number: 5,527,330
[45] Date of Patent: Jun. 18, 1996

[54] FLUID CUTTING INSTRUMENT

[75] Inventor: H. Jonathan Tovey, Milford, Conn.

[73] Assignee: United States Surgical Corporation, Norwalk, Conn.

[21] Appl. No.: 292,632

[22] Filed: Aug. 18, 1994

[51] Int. Cl.⁶ ................................................ A61B 17/00
[52] U.S. Cl. .......................... 606/167; 606/159; 604/43
[58] Field of Search .................... 606/159, 170, 606/167, 128; 604/22, 43; 241/1, 40, 606, 168

[56] References Cited

U.S. PATENT DOCUMENTS

| 1,889,425 | 11/1932 | Sorensen . |
| 3,590,813 | 7/1971 | Roszyk . |
| 3,811,795 | 5/1974 | Olsen . |
| 3,930,505 | 1/1976 | Wallach . |
| 3,993,054 | 11/1976 | Newman . |
| 4,024,966 | 5/1977 | Wallach . |
| 4,186,733 | 2/1980 | Mogaki . |
| 4,368,734 | 1/1983 | Banko . |
| 4,441,488 | 4/1984 | Macabee . |
| 4,690,672 | 9/1987 | Veltrup . |
| 4,694,828 | 9/1987 | Eichenbaum . |
| 4,935,006 | 6/1990 | Hasson . |
| 4,944,726 | 7/1990 | Hillal et al. . |
| 5,024,615 | 6/1991 | Buchel . |
| 5,037,431 | 8/1991 | Summers et al. . |
| 5,135,482 | 8/1992 | Neracher . |
| 5,261,883 | 11/1993 | Hood et al. . |
| 5,361,583 | 11/1994 | Huitema . |
| 5,370,609 | 12/1994 | Drasler et al. ........................ 606/159 |

FOREIGN PATENT DOCUMENTS

| 0175096A1 | 3/1986 | European Pat. Off. . |
| 0258901A2 | 3/1988 | European Pat. Off. . |
| 0411170A1 | 2/1991 | European Pat. Off. . |
| 044778A1 | 9/1991 | European Pat. Off. . |
| 0527312 | 2/1993 | European Pat. Off. ............... 606/159 |
| 0555549A1 | 8/1993 | European Pat. Off. . |

OTHER PUBLICATIONS

Transection of the Liver With a Water Jet, Bo G. Persson et al., pp. 267, 268.
Rheolytic Catheter for Percutaneous Removal of Thrombus, William J. Drasler et al., pp. 263–267.

Primary Examiner—Stephen C. Pellegrino
Assistant Examiner—William W. Lewis

[57] ABSTRACT

A cutting and suctioning instrument is disclosed for use in surgery which is adapted for coupling to an external high pressure fluid source and an external vacuum source, which comprises an irrigation tube configured for coupling to the external high pressure fluid source. The distal end of the irrigation tube forms a nozzle to direct the high pressure fluid in the form of a high pressure fluid stream. A suction tube is provided for coupling to the external vacuum source. The distal end is positioned opposite the nozzle of the irrigation tube and is configured to receive and suction away waste fluid and separated tissue. A method for cutting tissue is also disclosed.

18 Claims, 7 Drawing Sheets

FIG_7

FIG_8

FIG_12

FIG_13

FLUID CUTTING INSTRUMENT

BACKGROUND

1. Technical Field

This application relates to medical instruments for cutting tissue with high pressure fluid, and method of using such instruments in surgical procedures.

2. Description of the Related Art

Traditional instruments for cutting tissue, for example the scalpel, have known limitations and drawbacks which have spurred development of new instrumentation incorporating the latest technology. One such technology, the use of high pressure fluid to cut tissue, provides various benefits to the surgeon. For example, fluid cutters are inherently self-cooling and therefore minimize heat generated at the surgical site. Unlike many laser and electrosurgical tools, fluid cutters can be more readily controlled so as to minimize damage to surrounding tissue.

Fluid jet cutters focus pressurized fluid in the form of high pressure fluid stream which is directed by the operator to impact desired tissue. When impacted by the high pressure fluid stream, soft tissue is emulsified then suctioned from the surgical site. Laser and electrosurgical cutting instruments, in contrast, typically fragment tissue by ablation or electrothermal dissolution which may cause undesirable damage to surrounding tissue.

Surgical cutting procedures often require suctioning or aspiration of the surgical site to maintain proper visualization by the surgeon. Aspiration of the surgical site during these surgical procedures is generally performed by an assistant to the surgeon. Fluid cutting instruments that incorporate aspiration and removal of fragmented tissue from the surgical site eliminate the need for the aforementioned assistant.

It would be desirable to provide a fluid cutting instrument which shields or deflects surrounding tissue. It would also be desirable to maintain the maximum amount of space available at the operative site by limiting the number and size of the instruments necessary to perform the surgical procedure.

SUMMARY

A cutting and suctioning instrument is disclosed for use in surgery which is adapted for coupling to an external high pressure fluid source and an external vacuum source, which includes an irrigation tube with a proximal end configured for coupling to the external high pressure fluid source, and a distal end which forms a nozzle to direct the high pressure fluid flowing from the proximal end out of the nozzle in the form of a high pressure fluid stream.

The instrument also includes a suction tube having a proximal end which is configured for coupling to an external vacuum source while the distal end is positioned opposite the nozzle of the irrigation tube and is configured to receive and suction away waste fluid and separated tissue.

A shaft has a proximal end which is coupled to a handle, a distal end, and at least one bore configured to accommodate a portion of the irrigation and suction tubes therein. The shaft is configured for insertion through a trocar if desired.

In one embodiment, the irrigation and suction tubes extend distally out from the distal end of the shaft and are spaced from one another a distance exceeding the diameter of the shaft. In this embodiment, the instrument further includes a sleeve member circumferentially disposed around the shaft. The sleeve member is slidable along the shaft to cam the distal ends of the suction and irrigation tubes toward one another and into the interior of the sleeve member to allow the instrument to be inserted through the trocar.

In another embodiment, no external vacuum source is provided. Rather, the distal end of the suction tube is replaced with a backstop member forming a flanged portion having a backstop face. The proximal end is connected to the distal end of the shaft. The flanged portion is positioned opposite that of the nozzle of the irrigation tube such that the high pressure fluid stream is directed at the backstop face.

Further, in another embodiment, the cutting and suctioning instrument is adapted for coupling to an external high pressure fluid source and an external vacuum source. The instrument has an elongated body portion forming a notched portion adjacent its distal end. The body portion has at least one bore therethrough, and defines a suction chamber having an inlet and an outlet. The inlet is disposed at the distal end of the notched portion while the outlet is in communication with the external vacuum source to provide suctioning at the inlet.

An irrigation tube is disposed within the at least one bore and has a proximal end connected to the external high pressure fluid source. The irrigation tube further has a distal end disposed at the proximal end of the notched portion of the body portion. The irrigation tube is configured to channel high pressure fluid from the external high pressure fluid source to the distal end of the irrigation tube. Nozzle means is provided which is operatively associated with the distal end of the irrigation tube for emitting the high pressure fluid in the form of a high pressure fluid stream directed at the inlet of the suction chamber.

A surgical method is also disclosed for cutting tissue with an instrument in communication with a high pressure fluid source and a vacuum source. The method includes the steps of positioning the tissue to be cut between the nozzle and end of the suction tube, directing a narrow jet of high pressure fluid against the tissue to cut the tissue, and suctioning, substantially simultaneously to the directing step, waste fluid and separated tissue from the operative site.

BRIEF DESCRIPTION OF THE DRAWINGS

Preferred embodiments are described hereinbelow with reference to the drawings wherein.

DETAILED DESCRIPTION OF PREFERRED EMBODIMENTS

Figures 1, 2:
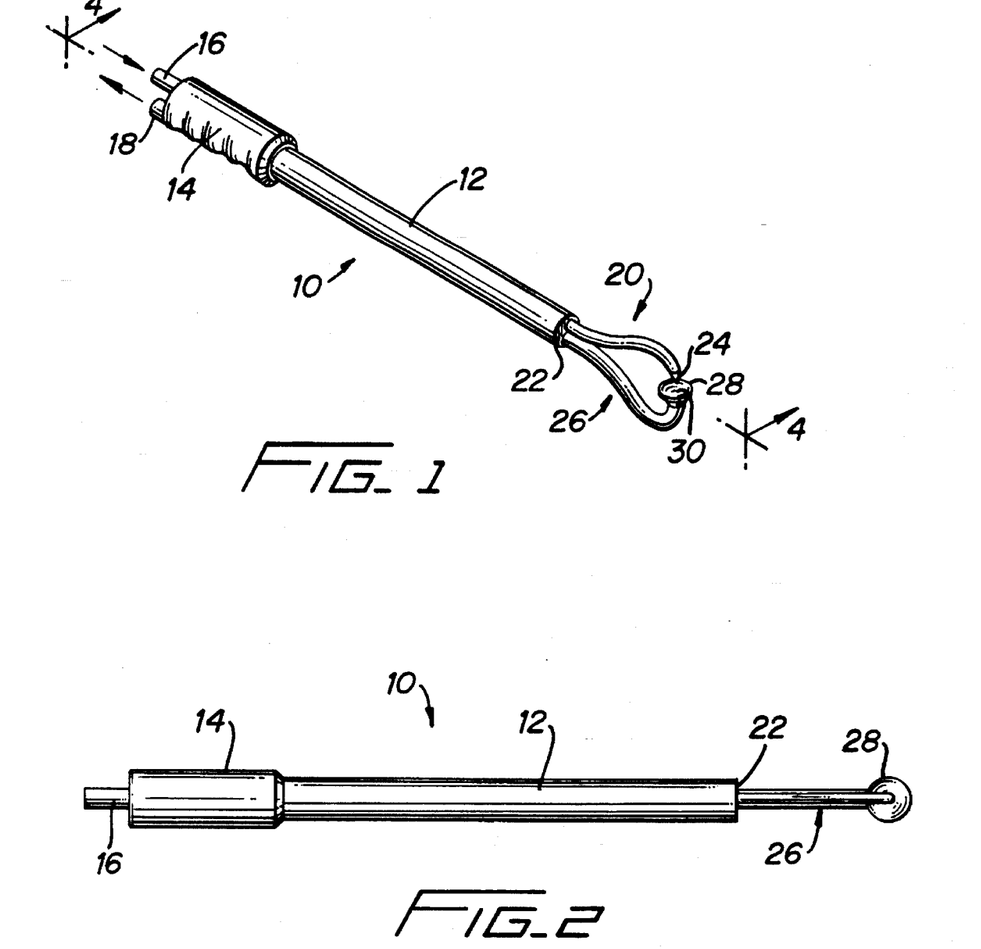
FIG. 1 is a perspective view of the fluid cutting instrument.
FIG. 2 is a bottom elevational view of the fluid cutting instrument.
Figure 3:
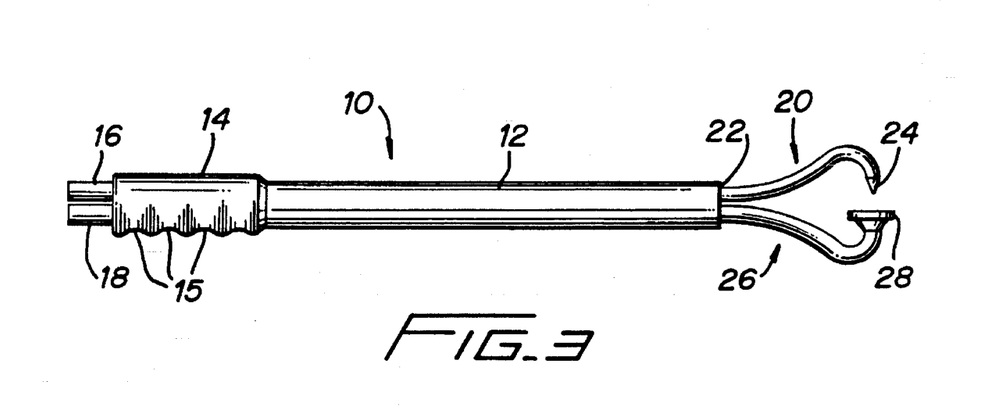
FIG. 3 is a side elevational view of the fluid cutting instrument.

Referring initially to FIG. 1, fluid cutting instrument 10 generally includes an elongated shaft 12, a handle 14, an irrigation tube 16, and a suction tube 18.

Referring to FIGS. 1–4, handle 14 is circumferentially attached to the proximal end of shaft 12 and is configured to be held by an operator to control the manipulation of fluid cutting instrument 10. As shown, the longitudinal axis of handle 14 is in axial alignment with the longitudinal axis of shaft 12. Handle 14 also has indentations 15 for accommodating the surgeons fingers.

Figure 4:
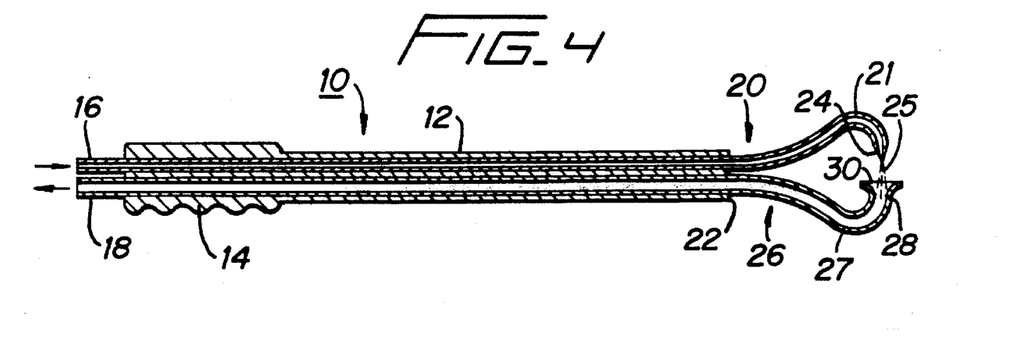
FIG. 4 is a side cross-sectional view of the fluid cutting instrument illustrating the irrigation and suction tubes therein.

As best seen in FIG. 4, irrigation tube 16 is partially disposed within a bore in shaft 12, and has distal portion 20 extending out from distal end 22 of shaft 12 forming irrigation nozzle 24. Shaft 12 is preferably of circular cross-section. Distal portion 20, as shown, includes arcuate region 21. Irrigation tube 16 is in communication with an external source of high pressure fluid connected to its proximal end (not shown), such that high pressure fluid, such as water or saline solution, is channeled through irrigation tube 16 and exits via irrigation nozzle 24 in the form of a high pressure stream 25. Preferably, the fluid is emitted in pulses at an angle to the longitudinal axis of the shaft 12. The preferred angle is 90°, however other angles are also contemplated.

With continued reference to FIG. 4, suction tube 18 is also disposed partially within a bore in shaft 12. Suction tube 18 has distal portion 26 extending from distal end 22 of the shaft 12 forming a flanged portion 28. Distal portion 26 includes arcuate portion 27 which curves in a direction opposite to the curve of arcuate region 21 of irrigation tube 16. Flanged portion 28 has a suction opening 30 positioned opposite irrigation nozzle 24 so that excess fluid and excised tissue are sucked through suction opening 30 and effectively discharged by an external suction source (not shown) in communication with and connected to the proximal end of suction tube 18. The suction opening 30 is enlarged to help prevent clogging.

Figure 5A:
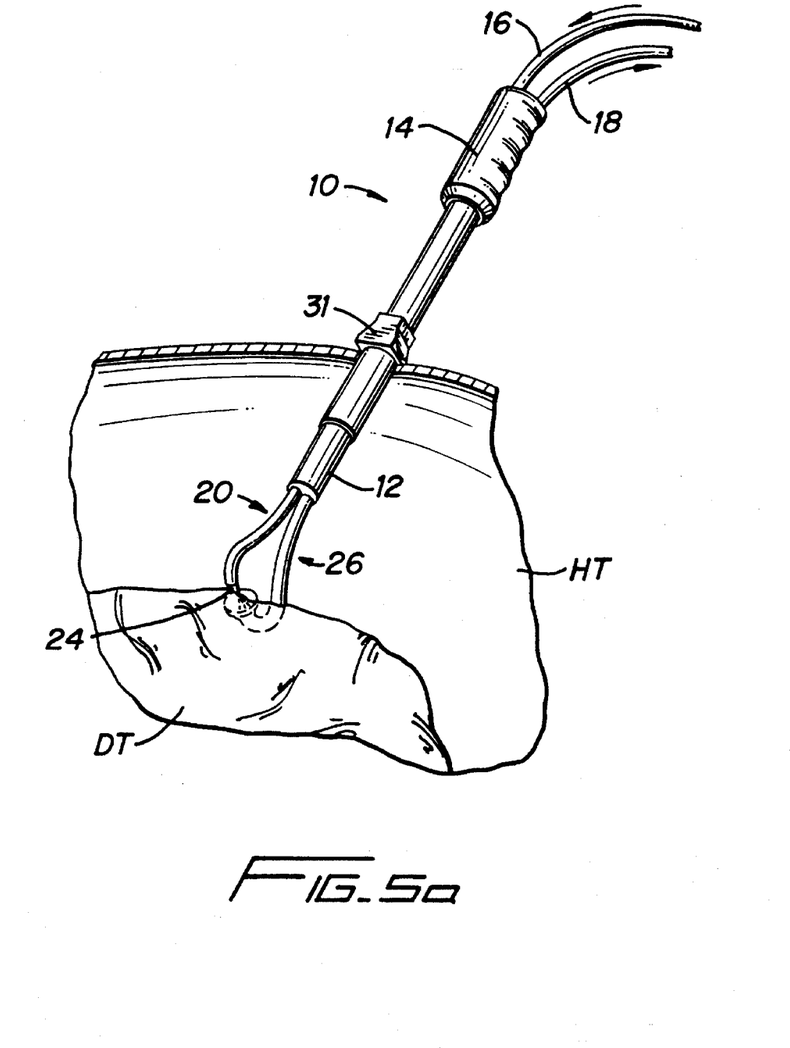
FIG. 5A is a perspective view of the fluid cutting instrument positioned at an operative site with tissue positioned between the irrigation tube and suction tube.
Figures 5B, 5C:
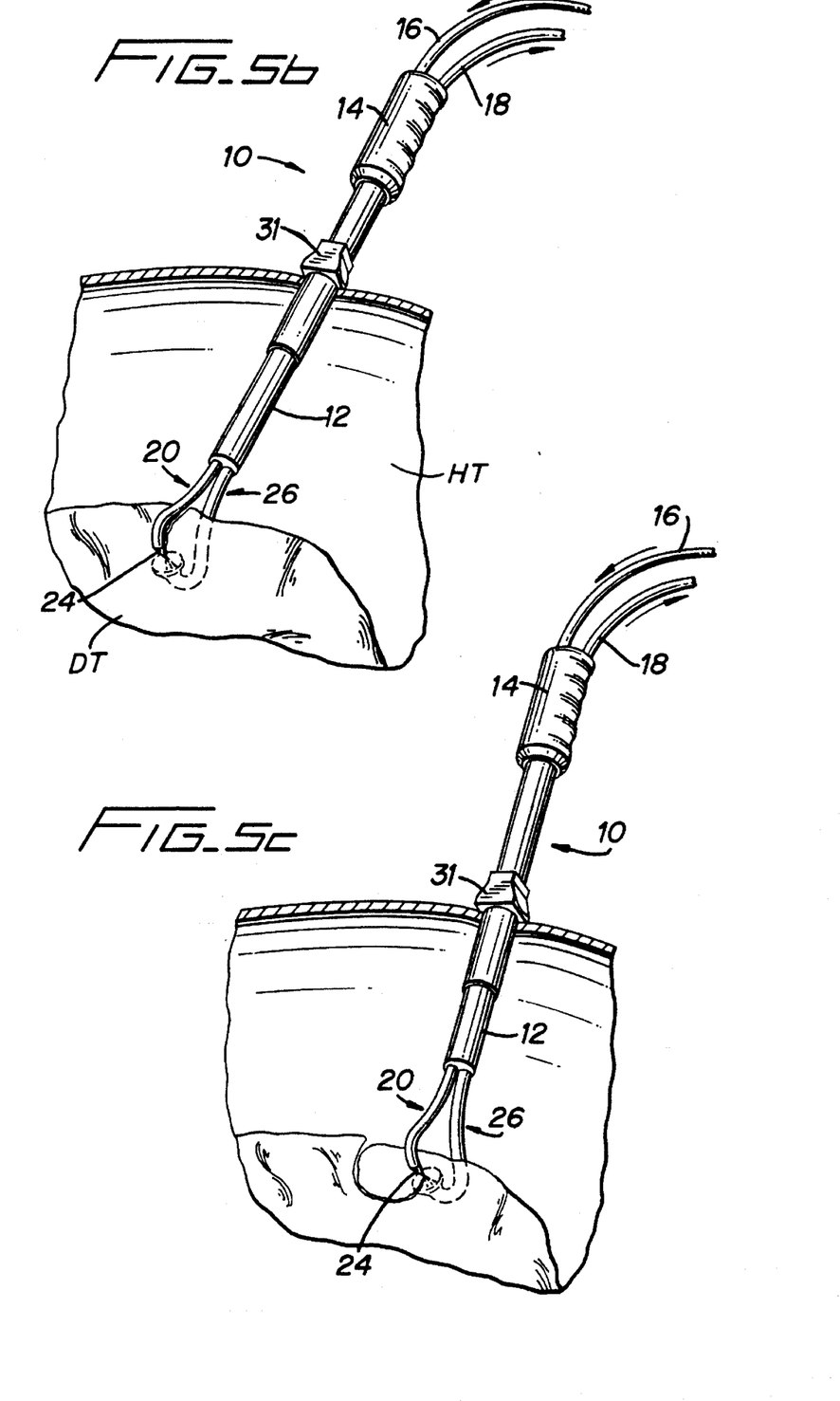
FIG. 5B is a perspective view of the fluid cutting instrument of FIG. 5A illustrating tissue partially cut by the instrument.
FIG. 5C is a perspective view of the fluid cutting instrument of FIG. 5B illustrating tissue being fully cut away from surrounding tissue.

Referring to FIGS. 5A–5C, a method according to the invention of using instrument 10 to cut diseased tissue DT away from healthy tissue HT will be described. Fluid cutting instrument 10 is inserted through a surgical port, for instance trocar 31, and positioned at the operative site. Diseased tissue DT is initially positioned between irrigation is nozzle 24 and flanged portion 28. High pressure stream 25 is then emitted from irrigation nozzle 24 and into contact with diseased tissue DT. Substantially simultaneously to the emitting of high pressure stream 25, suctioning of the operative site by suction tube 18 is externally initiated. Referring to FIGS. 5B–5C, instrument 10 is manipulated by the operator to further excise diseased tissue DT from healthy tissue HT until the diseased tissue DT is fully excised from healthy tissue HT and suctioned away from the operative site. The surgical procedure having been completed, instrument 10 can be withdrawn from the patient via trocar 31.

As will be appreciated, the trocar utilized can either have a diameter sufficiently large to allow insertion of irrigation nozzle 124 and flanged portion 128 therethrough. Alternatively, the distal portion 120 of irrigation tube 116 and distal portion 126 of suction tube 118 can be made sufficiently flexible to flex inwardly towards one another as the instrument is inserted through the trocar cannula. This allows a smaller diameter trocar to be utilized.

It is also contemplated that instrument 110 be used in open procedures, i.e., non-endoscopic procedures.

Figure 6A:
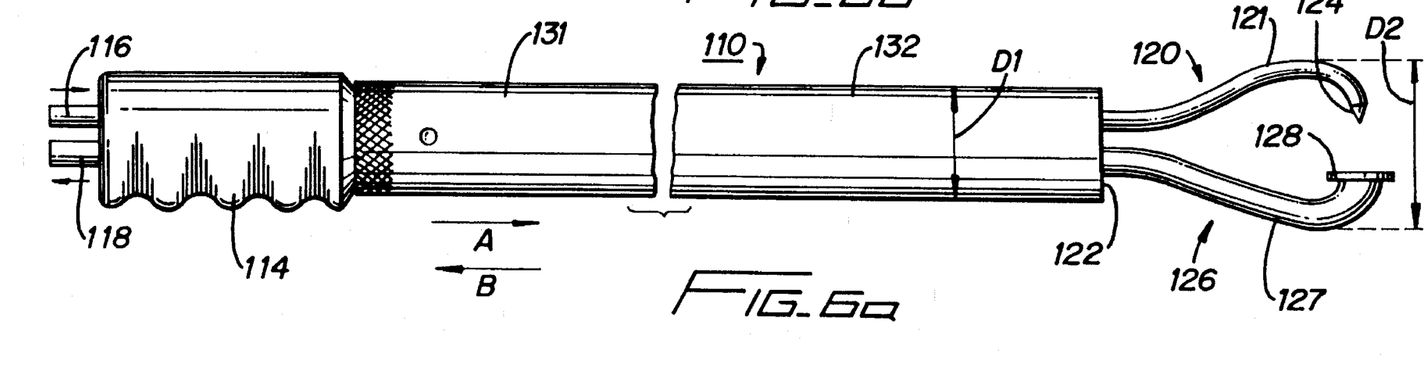
FIG. 6A is a side elevational view of an alternate embodiment of a fluid cutting instrument illustrating the sleeve member in a fully proximal position.
Figure 6B:
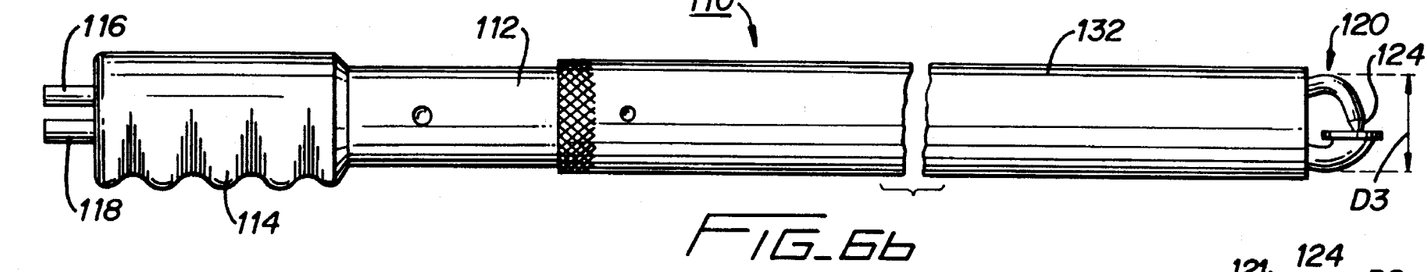
FIG. 6B is a side elevational view of the fluid cutting instrument of FIG. 6A illustrating the sleeve member in a partially distal position.
Figure 6C:
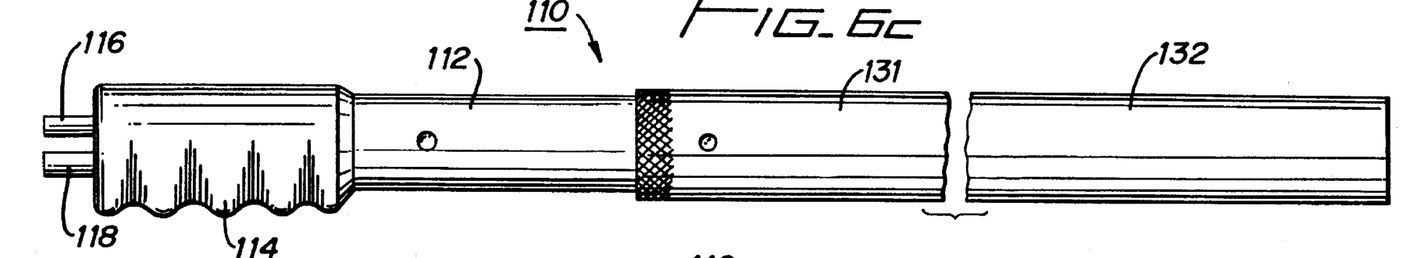
FIG. 6C is a side elevational view of the fluid cutting instrument of FIG. 6B illustrating the sleeve member in a fully distal position.

In an alternate embodiment illustrated in FIGS. 6A–6C, instrument 110 includes handle 114 and irrigation and suction tubes 116 and 118 similar to that described in the embodiment of FIGS. 1–4. In this embodiment, sleeve member 132, preferably cylindrical in configuration, is circumferentially disposed around shaft 112. Sleeve member 132 is slidable along shaft 112 in the direction of arrows A & B such that when sleeve member 132 is moved distally toward distal portions 120 and 126 of tube 116 and 118 respectively, sleeve member 132 contacts arcuate portions 121 and 127 of distal portions 120 and 126 to cam distal portions 120 and 126 towards one another. (The outermost surface of arcuate portions 121, 127 are initially spaced a distance D2) The camming of distal portions 120 and 126 places them into a position in which the outermost surfaces are spaced from one another a distance D3 that is less than the internal diameter D1 of sleeve member 132 allowing sleeve member 132 to fully enclose these portions. With sleeve member 32 fully moved to its distalmost position of FIG. 6C, the instrument 110 can be easily inserted or withdrawn through a trocar to or from the surgical site without interference.

Therefore, in use, sleeve 132 would be slid distally (longitudinally) to cam distal portions 120, 126 toward one another and to fully enclose nozzle 124 and flange 128. The instrument is then inserted through the trocar adjacent to the surgical site. The surgeon then grasps the proximal portion 31 of sleeve 132, which remains outside the trocar (not shown) due to the length of sleeve 132, and slides it proximally in the direction of arrow B to expose nozzle 124 and flange 128 for placement around the tissue to be excised. The high pressure fluid is then applied to the surgical site via irrigation tube 116, with the excess fluid and tissue suctioned through suction tube 118. After completion of the procedure, sleeve 133 can once again be slid over nozzle 127 and flange 128 to facilitate removal through the trocar cannula.

Figure 7:
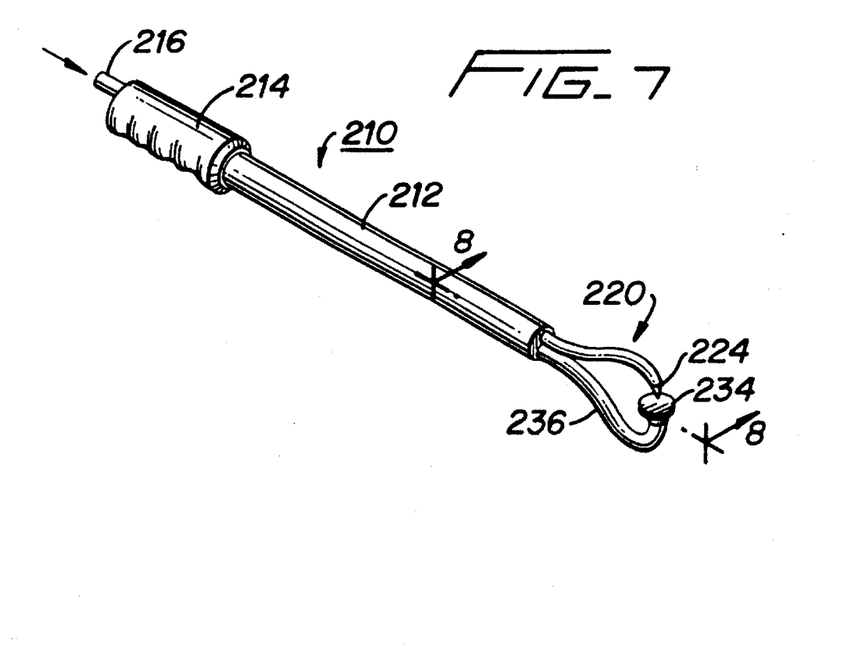
FIG. 7 is a perspective view of another alternate embodiment of a fluid cutting instrument having a backstop.
Figure 8:
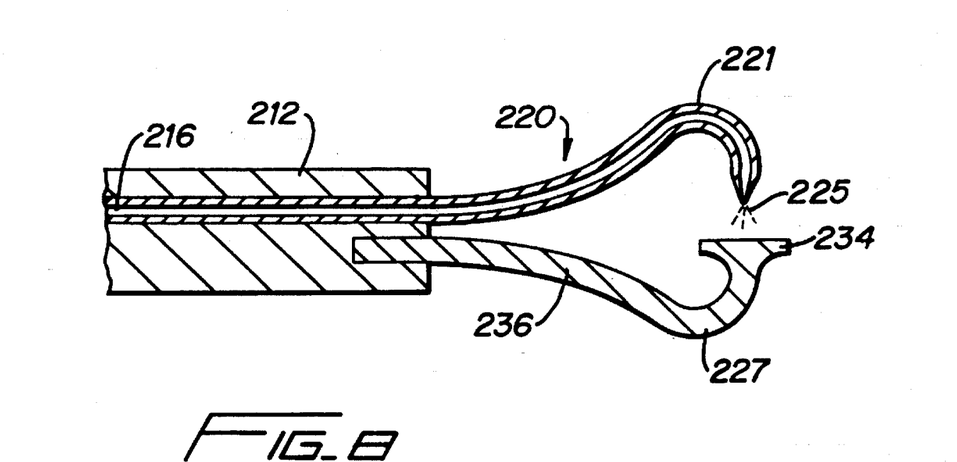
FIG. 8 is a cross-sectional view of the distal end of the fluid cutting instrument of FIG. 7.
Figure 9:
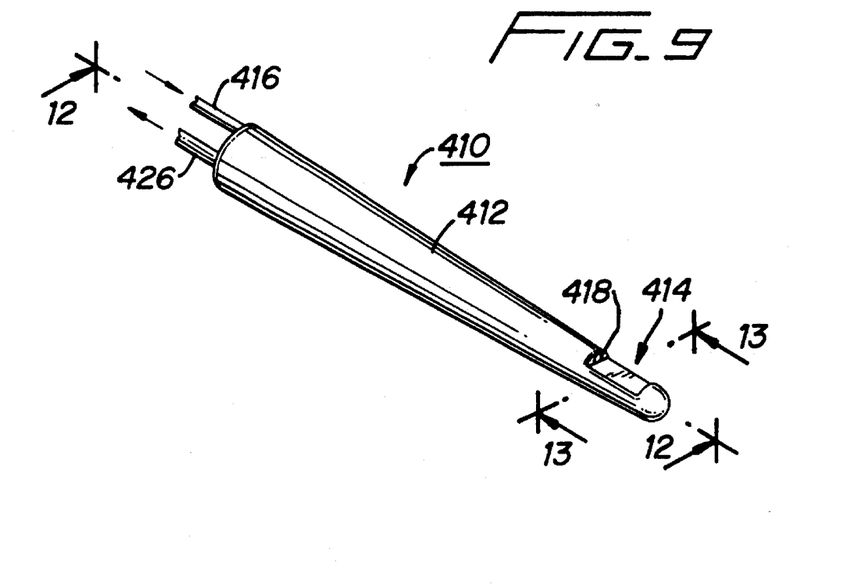
FIG. 9 is a perspective view of yet another embodiment of a fluid cutting instrument.
Figure 10:
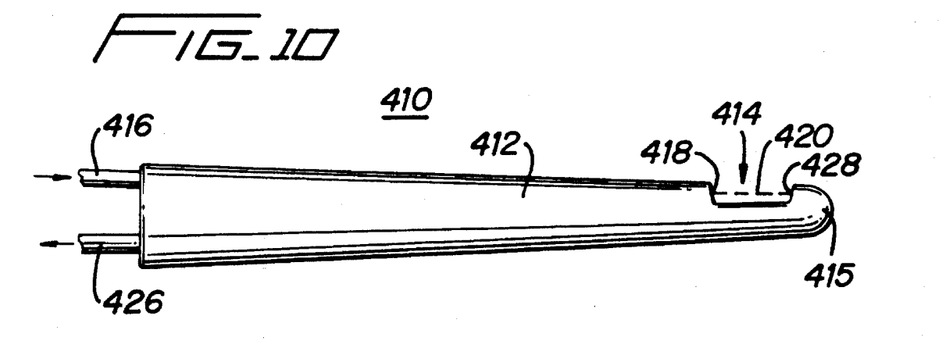
FIG. 10 is a side elevational view of the fluid cutting instrument of FIG. 9 illustrating the fluid stream.
Figure 11:
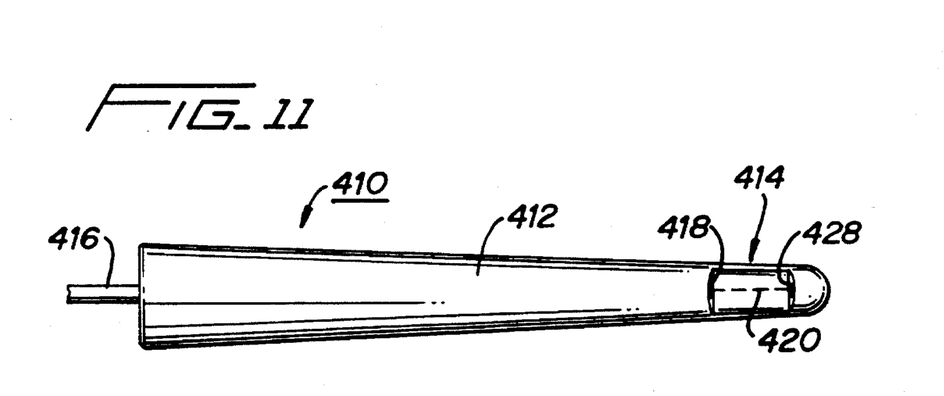
FIG. 11 is a top elevational view of the fluid cutting instrument of FIG. 10.

In another embodiment of the present invention as illustrated in FIGS. 7–8, instrument 210, similar to the embodiment of FIG. 1, includes handle grip 214 and elongated shaft 212. However, in this embodiment only an irrigation tube 216 is provided. A backstop support member 236 is connected to shaft 212 by conventional means such as welding, and forms a backstop plate 234 at the distal end which is positioned opposite that of nozzle 224. Backstop plate 234 preferably includes a substantially planar surface positioned perpendicular to fluid stream 225. This backstop plate 234 functions to hold the tissue as well as deflect fluid stream 25 such that surrounding tissue is not inadvertently harmed. Backstop support 236 has arcuate portion 227 curved in a direction opposite to the curve of arcuate portion 221 of irrigation tube 216. Backstop support 236 can be composed of a rigid material or alternatively of a flexible material to allow flexing during the procedure as well as flexing during insertion and withdrawal through a trocar cannula, if desired. Backstop plate 234 can alternatively have a recess to receive the end of nozzle 24 when cammed towards each other during insertion through a trocar.

Figure 12:
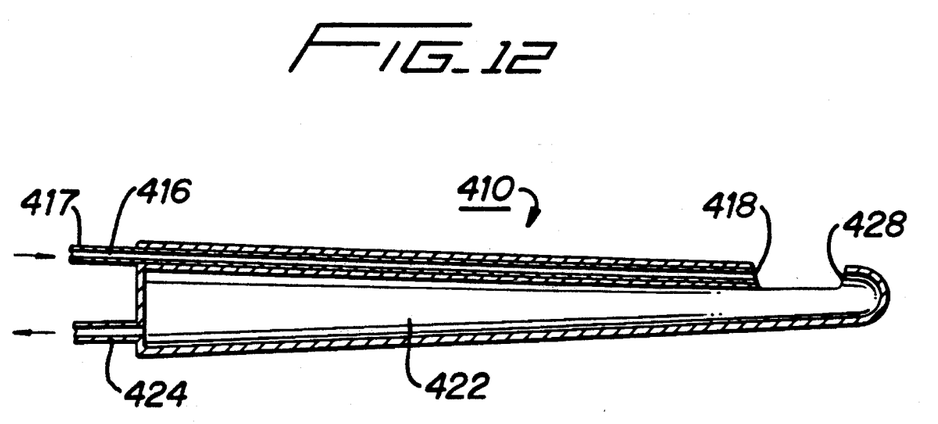
FIG. 12 is a cross-sectional view taken along line 12—12 of FIG. 9 illustrating the irrigation and suction tubes.
Figure 13:
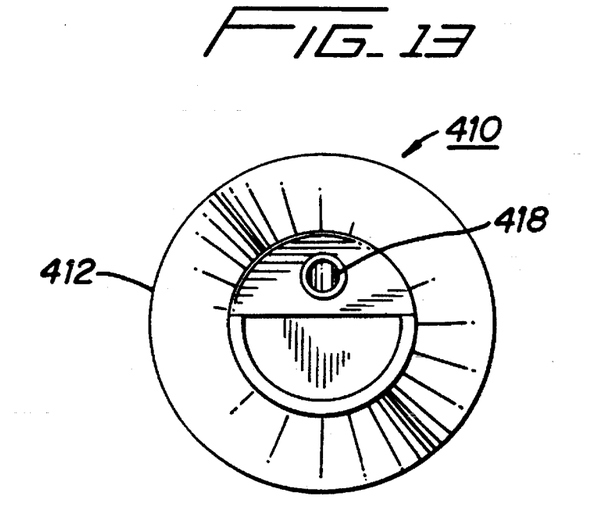
FIG. 13 is cross-sectional view taken along line 13—13 of FIG. 9 illustrating the nozzle of the irrigation tube.

In yet another embodiment of the present invention as illustrated in FIGS. 9–13, fluid cutting instrument 410 is shown. Instrument 410 has an elongated body portion 412 defining a notched portion 414 at the distal end portion and terminating in a rounded blunt tip 415. Body portion 412 also progressively decreases in diameter toward the distal end, however alternately it could be for example, of uniform diameter throughout its length. As best seen in FIG. 12, irrigation tube 416 is partially disposed through a bore in body portion 412. Irrigation tube 416 is in communication with an external source of high pressure fluid (not shown) connected to the proximal end 417 of irrigation tube 416 such that the high pressure fluid is channeled through irrigation tube 416 and exits via irrigation nozzle 418 positioned at the proximal end of notched portion 414 in the form of high pressure stream 420. Body portion 412 further defines a suction chamber 422 having a suction outlet 424 in suction tube 426. Suction chamber 422 is in communication with an external vacuum source (not shown) via suction tube 426 being linked with the vacuum source and connected to suction outlet 424. Suction chamber 422 defines a suction opening 428 positioned at the distal end of notched portion 414 opposite that of irrigation nozzle 418 so that waste fluid and separated tissue are suctioned through suction opening 128 and effectively discharged by the suction source.

In operation, tissue is positioned in notched portion 414 and high pressure fluid is ejected through irrigation 418 to excise the tissue. The excess fluid and separated tissue are suctioned through opening 428 and through chamber 422. The chamber preferably increases in thickness (diameter) towards the proximal end to help prevent clogging. When the tissue is fully excised, the fluid stream travels directly through opening 428 rather than independently impinging on healthy tissue, until the user shuts off the fluid flow. The instrument 414 can be used in both open and in laparoscopic procedures.

It will be understood that various modifications may be made to the embodiment disclosed herein. For example, a different handle configuration can be utilized or a pivoting handle can be provided to slide the sheath in the embodiment lo of FIGS. 6A–6C. Therefore, the above description should not be construed as limiting, but merely as exemplifications of preferred embodiments. Those skilled in the art will envision other modifications within the scope and spirit of the claims appended hereto.

What is claimed is:

1. A surgical instrument for cutting tissue and suctioning, the instrument adapted for coupling to an external high pressure fluid source and an external vacuum source, the instrument comprising:

an elongated shaft defining a longitudinal axis and having a proximal end portion and a distal end portion;

an irrigation tube at least partially disposed within the elongated shaft and having a proximal end portion and a distal end portion, the proximal end portion configured for coupling to an external high pressure fluid source, the distal end portion disposed beyond the elongated shaft and defining a nozzle portion to direct a stream of high pressure fluid supplied by the high pressure fluid source to cut tissue; and a suction tube at least partially disposed within the elongated shaft and having a proximal end portion and a distal end portion, the proximal end portion configured for coupling to an external vacuum source, the distal end portion disposed beyond the elongated shaft and positioned and oriented in an opposed spaced relation relative to the nozzle portion of the irrigation tube such that body tissue is positionable therebetween, the distal end portion having a vacuum opening therein configured to receive and suction away waste fluid and separated tissue.

2. The instrument of claim 1 wherein the elongated shaft includes at least one axial bore configured to accommodate a portion of at least one of the irrigation and suction tubes.

3. The instrument of claim 2 further comprising a handle connected to the proximal end of the shaft, the handle configured to be held by an operator to control manipulation of the instrument.

4. The instrument according to claim 1 wherein the nozzle portion of the irrigation tube is angularly oriented relative to the longitudinal axis of the elongated shaft such that the stream of high pressure fluid supplied by the high pressure fluid source is emitted at an angle relative to the longitudinal axis of the elongated shaft.

5. A surgical instrument for cutting tissue and suctioning, the instrument adapted for coupling to an external high pressure fluid source and an external vacuum source, the instrument comprising:

an elongated shaft defining a longitudinal axis and having proximal and distal ends, the shaft defining at least one axial bore therein;

an irrigation tube at least partially positioned within the one axial bore of the shaft and having proximal and distal ends, the proximal end configured for coupling to an external high pressure fluid source, the distal end forming a nozzle to direct high pressure fluid from the high pressure fluid source to cut tissue;

a suction tube at least partially positioned within the one axial bore of the shaft and having proximal and distal ends, the proximal end configured for coupling to an external vacuum source, the distal end positioned opposite the nozzle of the irrigation tube and configured to receive and suction away waste fluid and separated tissue; and a sleeve member positioned on the shaft, the sleeve member reciprocally longitudinally movable relative to the shaft between a proximalmost and a distalmost position thereof wherein movement of the sleeve member towards the distalmost position causes inner surfaces of the sleeve member to engage and bias at least the distal ends of the suction and irrigation tubes toward one another.

6. A surgical instrument for cutting tissue and suctioning, the instrument adapted for coupling to an external high pressure fluid source and an external vacuum source, the instrument comprising:

an elongated shaft defining a longitudinal axis and having proximal and distal ends, the shaft defining at least one axial bore therein;

an irrigation tube at least partially positioned within the one axial bore of the shaft and having proximal and distal ends, the proximal end configured for coupling to an external high pressure fluid source, the distal end forming a nozzle portion to direct high pressure fluid from the high pressure fluid source to cut tissue, the nozzle portion being aligned such that the stream of high pressure fluid is emitted at an angle of approximately 90° relative to the longitudinal axis of the shaft;

a suction tube at least partially positioned within the one axial bore of the shaft and having proximal and distal ends, the proximal end configured for coupling to an external vacuum source, the distal end positioned opposite the nozzle of the irrigation tube and configured to receive and suction away waste fluid and separated tissue.

7. A surgical instrument for cutting tissue and suctioning, the instrument adapted for coupling to an external high pressure fluid source and an external vacuum source, the instrument comprising:

an elongated shaft for insertion through a trocar and defining a longitudinal axis, the shaft having a proximal end and a distal end;

an irrigation tube supported by the elongated shaft and having a proximal end and a distal end, the proximal end configured for coupling to an external high pressure fluid source, the distal end forming a nozzle to direct a stream of high pressure fluid from the high pressure fluid source to cut tissue; and a suction tube supported by the elongated shaft and having a proximal end and a distal end, the proximal end configured for coupling to the external vacuum source, the distal end positioned opposite the nozzle of the irrigation tube and configured to receive and suction away waste fluid and separated tissue.

8. A surgical instrument for cutting tissue with high pressure fluid, which comprises:

an elongated shaft defining a longitudinal axis and having a proximal end and a distal end, the shaft having a bore extending therethrough;

an irrigation tube extending through the bore of the shaft, the irrigation tube having a proximal end and a distal end, the proximal end configured for coupling to an external high pressure fluid source, the distal end forming a nozzle to direct high pressure fluid from the high pressure fluid source out of the nozzle in the form of a high pressure fluid stream; and a backstop member extending from the distal end of the shaft and positioned opposite the nozzle of the irrigation tube such that the high pressure fluid stream is directed at the backstop member, the backstop member being spaced from the nozzle such that tissue is positionable therebetween, the backstop member supporting the tissue during emission of the high pressure fluid stream from the nozzle.

9. The instrument according to claim 8 wherein the nozzle is aligned such that the high pressure fluid stream is emitted at an angle of approximately 90° relative to the longitudinal axis of the shaft.

10. The instrument according to claim 9 wherein the backstop member forms a flanged portion, the flanged portion including a substantially planar surface positioned opposite to the nozzle of the irrigation tube such that the high pressure fluid stream is directed to the flanged portion.

11. The instrument according to claim 8 wherein the nozzle of the irrigation tube is angularly oriented relative to the longitudinal axis of the elongated shaft such that the high pressure fluid stream emitted by the nozzle is oriented at an angle relative to the longitudinal axis of the elongated shaft.

12. A surgical instrument for cutting and suctioning, the instrument adapted for coupling to an external high pressure fluid source and an external vacuum source, which comprises:

a body portion defining a longitudinal axis and having at least one bore extending therethrough defining a suction passage having an inlet and an outlet, the outlet in communication with an external vacuum source to provide suctioning at the inlet;

an irrigation passage disposed within the body portion and connected to an external high pressure fluid source at a proximal end and having a distal end where high pressure fluid supplied by the external high pressure fluid source is emitted; and a notched portion formed in the body portion and having a proximal end in communication with the irrigation passage and a distal end in communication with the suction passage, the notched portion dimensioned to accommodate body tissue therein such that the body tissue is between the distal end of the irrigation passage and the inlet of the suction passage.

13. The instrument according to claim 12 further comprising nozzle means operatively associated with the distal end of the irrigation passage for emitting the high pressure fluid in the form of a high pressure fluid stream directed at the inlet of the suction passage.

14. The instrument according to claim 13, wherein the nozzle directs fluid in a direction substantially parallel to the longitudinal axis of the body portion.

15. The instrument according to claim 14, wherein the body portion is tapered towards the distal end.

16. A surgical method for cutting tissue comprising the steps of:

providing an instrument including an elongated member having an irrigation tube with proximal and distal end portions, the proximal end portion coupled to an external high pressure fluid source, the distal end portion disposed beyond the elongated member and defining a nozzle to direct the high pressure fluid in the form of a high pressure fluid stream, a suction tube having proximal and distal end portions, the proximal end portion couplable to an external vacuum source, the distal end portion disposed beyond the elongated member and positioned opposite the nozzle of the irrigation tube, the distal end portion having a vacuum opening configured to receive and suction away waste fluid and separated tissue;

positioning tissue to be cut between the nozzle of the irrigation tube and the distal end portion of the suction tube;

directing the high pressure fluid against the tissue; and suctioning waste fluid and separated tissue through the vacuum opening.

17. A surgical method for cutting tissue comprising the steps of:

providing an instrument having an elongated body portion forming a notched portion with a proximal end and a distal end, an inlet disposed at the distal end of the notched portion and in communication with an external vacuum source to provide suctioning at the inlet; an irrigation tube coupled to an external high pressure fluid source and to the proximal end of the notched portion; and nozzle means operatively associated with the irrigation tube for emitting the high pressure fluid in the form of a high pressure fluid stream directed at the inlet;

positioning the tissue to be cut within the notched portion of the elongated body and between the nozzle means and the inlet;

directing a narrow jet of high pressure fluid against the tissue; and suctioning waste fluid and separated tissue through the inlet.

18. The method according to claim 17 wherein the suctioning step is performed substantially simultaneously to the directing step.

* * * * *